United States Patent [19]
Gandi et al.

[11] Patent Number: 5,474,542
[45] Date of Patent: Dec. 12, 1995

[54] CATHETER HAVING IMPERFORATE PROTECTIVE BARRIER AND METHOD FOR MAKING AND USING THE SAME

[76] Inventors: Robert A. Gandi, 299 W. 12th St., New York, N.Y. 10014; Gianfranco U. Meduri, 2867 Belfort Dr., Germantown, Tenn. 38138; David S. Ostrowski, 94 Tuft Hill Rd., N. Grosvenordale, Conn. 06255

[21] Appl. No.: 130,290

[22] Filed: Oct. 1, 1993

[51] Int. Cl.$^6$ ......................................... A61M 5/32
[52] U.S. Cl. ............................. 604/265; 604/280
[58] Field of Search ............................ 604/265, 264, 604/263, 280, 266, 285; 424/422–426

[56] References Cited

U.S. PATENT DOCUMENTS

| | | |
|---|---|---|
| 3,736,939 | 6/1973 | Taylor . |
| 3,800,798 | 4/1974 | Winkler . |
| 4,235,244 | 11/1980 | Abele et al. . |
| 4,936,835 | 6/1990 | Haaga ........................ 604/265 |
| 5,066,278 | 11/1991 | Hirschberg et al. ............. 604/265 X |
| 5,201,724 | 4/1993 | Hukins et al. .................. 604/265 |

*Primary Examiner*—John D. Yasko
*Attorney, Agent, or Firm*—Darby & Darby

[57] ABSTRACT

A catheter has a distal end which is to be positioned through potentially contaminated tissue within a patient to a desired site, and a proximal end. The catheter has at least one fluid lumen extending between the distal end and the proximal end. The fluid lumen provides fluid communication between the desired site and the proximal end. A removable protective barrier is positioned within the fluid lumen at its distal end. The protective barrier is made from a biocompatible material and selectively occludes the distal end of the fluid lumen so that entry of the contaminated tissue, prior to the distal end of the catheter reaching the desired site, is prevented.

20 Claims, 5 Drawing Sheets

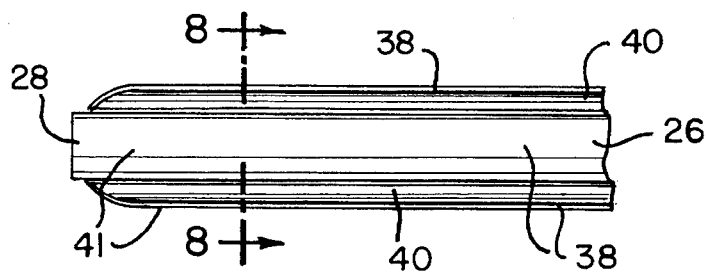
FIG. 7
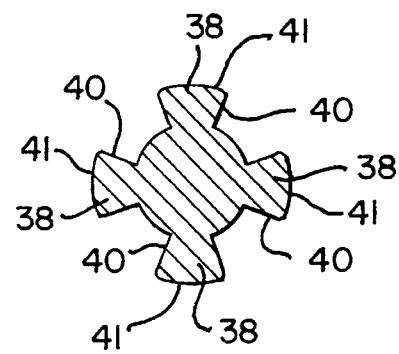
FIG. 8
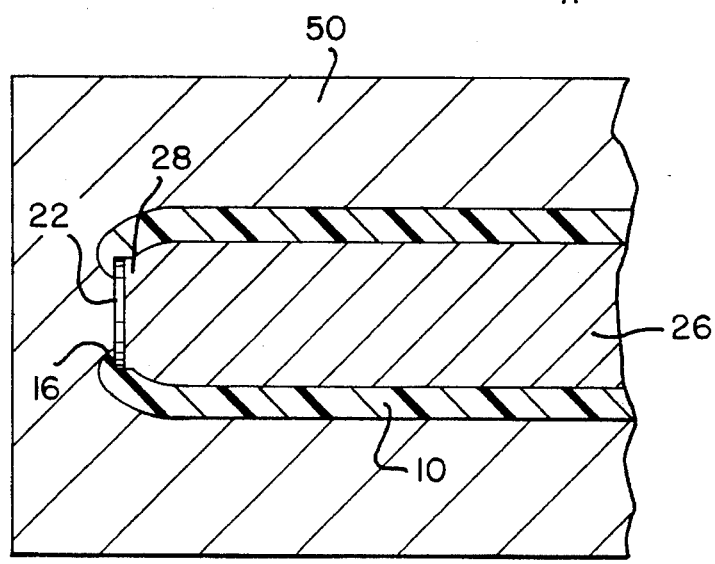
FIG. 9
FIG. 10
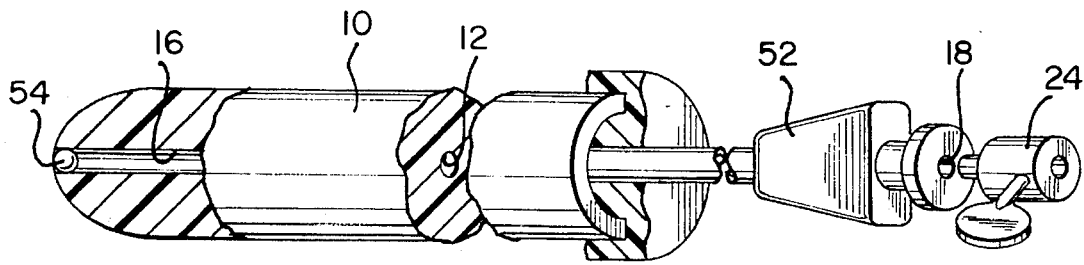

CATHETER HAVING IMPERFORATE PROTECTIVE BARRIER AND METHOD FOR MAKING AND USING THE SAME

FIELD OF THE INVENTION

The invention relates to catheters of the type having at least one fluid passage and including a removable barrier which protects a distal end of the fluid passage from contamination, especially as the catheter is inserted into a patient. The invention additionally includes various methods for applying such a protective barrier to the distal end of catheters and a method of using the catheter having such a protective barrier during certain medical procedures.

BACKGROUND OF THE INVENTION

Many surgical procedures require the use of catheters to provide local fluid communication to a particular site within a patient. Such fluid communication may provide means for administering medication directly to the site, or may provide a pressure relief passage to relieve gas or fluid pressure generated within the body cavity. Numerous other uses of catheters are commonplace in modern medicine.

Certain medical procedures require the use of catheters to obtain biological samples of an infected site of the patient. In this way, the cause of certain medical conditions and ailments may be identified and subsequently properly treated.

During their placement, however, these catheters must typically traverse contaminated areas and therefore have the potential of carrying some contaminated material to a desired site which is intended for treatment and/or diagnosis. The unexpected contamination of the desired site may cause inaccuracies in the diagnosis and therefore also in the prescribed treatment.

Moreover, as any open-ended catheter is forced through body tissue, the relatively sharp rim of the tubular opening of its fluid lumen often "cores" a portion of the tissue which results in the clogging of the fluid lumen. The tissue lodged within the fluid lumen either prevents fluid flow through the lumen or is inadvertently dislodged into the body once positive fluid pressure is applied. Once dislodged within a patient's body, such loose tissue pieces create, at the very least, undesirable and unnecessary concern. The dislodged "cored" tissue can contaminate and damage healthy tissue, cause numerous complications and in some situations, such as an embolus carried by the blood stream, the tissue piece may even result in the patient's death.

To help prevent the accidental spread of infection throughout a patient's body catheters have been proposed wherein the distal opening of the catheter is covered with a water-soluble cap. One such protective cap is disclosed by U.S. Pat. No. 3,736,939 issued to Taylor. The cap is primarily used to prevent the catheter from "coring" the tissue as it is forced through a patient's body. The cap, which provides a rounded distal end to the catheter, dissolves within the body after a predetermined period. Once the cap dissolves, the fluid passage of the catheter is exposed, thereby allowing fluid communication with the body tissue. Unfortunately, the cap disclosed in U.S. Pat. No. 3,736,939 and other similar caps of the prior art are inherently bulky and thereby restrict the degree of flexibility, maneuverability and accessibility of the catheter within the patient or within other surgical instruments used in certain medical procedures, such as a bronchoscope used to diagnosis and treat pulmonary diseases.

A common medical procedure for diagnosing pulmonary diseases, specifically pneumonia, includes the bronchoalveolar lavage (BAL) of a lung segment. In this procedure, the tip of a fiberoptic bronchoscope is wedged into a sampling position in the airway of a lung segment. Lavage fluid is then introduced into, and then removed from, the lung segment of interest. Material collected from the lung segment along with the retrieved lavage fluid can yield important diagnostic information regarding a particular infection or condition.

Unfortunately, in order for the bronchoscope to reach the bronchial tree, it must traverse the oropharynx or the endotracheal tube where resident bacteria are likely to be introduced into the open distal-end suction channel of the instrument, usually in the form of mucus. Once in position, as the lavage solution is passed directly through the suction channel of the bronchoscope, the "cored-plug" of mucus will be forced from the suction channel and directly into the lung segment being sampled. The foreign mucus will contaminate the lung segment and the lavage solution, and render any resulting diagnostic data frequently inaccurate.

A protected catheter is disclosed in a medical paper entitled "PROTECTED BRONCHOALVEOLAR LAVAGE, A New Bronchoscopic Technique to Retrieve Uncontaminated Distal Airway Secretions", written by G. Umberto Meduri, David H. Beals, Amado G. Maijub, and Vickie Baselski, dated April, 1991. The catheter disclosed by this paper includes a thin polyethylene glycol diaphragm formed across its distal tip "to prevent contaminants from entering the system". The paper fails to disclose the method for forming the thin protective diaphragm.

In another related procedure, a balloon-tipped catheter is passed through the suction channel of the bronchoscope. The catheter is positioned within the airway of a lung segment to be sampled. The balloon of the catheter is inflated to isolate one particular lung segment from the others. Lavaging is then performed through the fluid lumen of the balloon-tipped catheter. Unfortunately, a similar problem occurs as the catheter passes through the suction channel of the bronchoscope. The unprotected distal end of the fluid lumen of the catheter will "core" through the mucus-borne contaminants located at the distal end of the suction lumen, resulting in similarly contaminated sampling and inaccurate diagnostic data.

In several studies, oropharyngeal and tracheobronchial contaminants, which are present in high concentration in the upper respiratory tract of patients, were frequently found in BAL specimens taken from the patients who were not otherwise infected. Contamination of bronchoalveolar lavage from upper respiratory tract secretions using these prior art non-protected techniques, has limited the use of bronchoalveolar lavage in diagnosing bacterial pneumonia.

Therefore, it is an object of the invention to provide a device, and a method for its use, which effectively eliminates the above mentioned "coring" problems associated with prior art devices.

It is another object of the invention to provide a device and method for its use which effectively decreases or eliminates contamination of the respiratory tract secretions retrieved with BAL.

It is another object of the invention to provide a catheter which retains its non-contaminated integrity for fluid communication even after traversing contaminated areas.

SUMMARY OF THE INVENTION

A catheter has a distal end which is to be positioned through potentially contaminated fluid and/or tissue within a patient to a desired site, and a proximal end comprises at least one fluid lumen extending between the distal end and the proximal end. The fluid lumen provides fluid communication between the desired site and the proximal end. A selectively removable protective barrier is positioned within the fluid lumen at its distal end. The protective barrier is made from a biocompatible material and selectively occludes the distal end of the fluid lumen so that entry of the contaminated fluid and/or tissue, prior to the distal end of the catheter reaching the desired site, is prevented.

BRIEF DESCRIPTION OF THE DRAWINGS

FIG. 7 is a partial, side view of a mandrel, in accordance with another embodiment of the invention;

FIG. 8 is a sectional view of the mandrel of FIG. 7 taken along the lines 8—8;

FIG. 9 is a partial, sectional view of an alignment device showing a catheter in a membrane-receiving position, in accordance with another embodiment of the invention;

FIG. 10 is a partial, sectional perspective view of a catheter having a pellet shaped sealing plug located in its fluid lumen, in accordance with yet another embodiment of the invention;

DETAILED DESCRIPTION OF THE INVENTION

Figure 1:
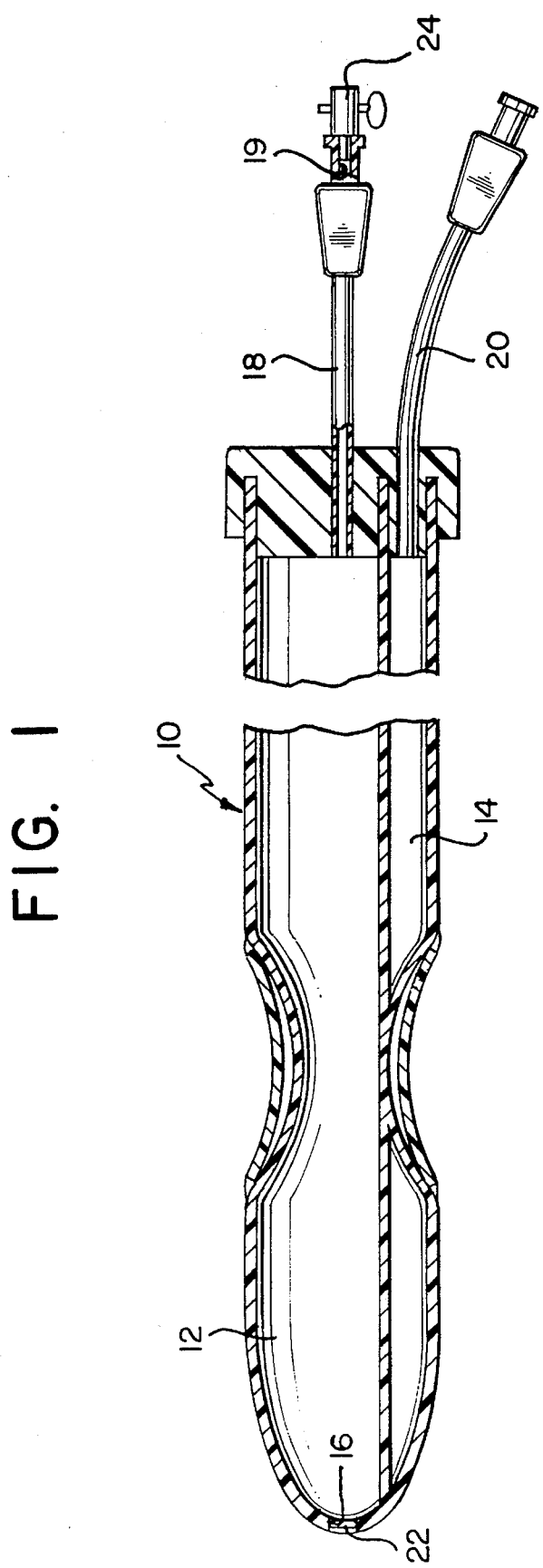
FIG. 1 is a partial sectional side view of a catheter having a protective membrane formed across a distal opening, in accordance with one embodiment of the invention.

Referring to FIG. 1, a balloon tipped catheter 10 in accordance with the invention is illustrated having a main fluid lumen 12, a balloon inflation lumen 14, a forward-facing distal opening 16, a proximal main fluid conduit 18 and a proximal balloon-fluid inlet 20.

The balloon-tipped catheter 10 shown in FIG. 1 has been chosen as an exemplary body-entering conduit in accordance with one embodiment of the invention. Any body-entering or body-piercing conduit having a fluid lumen may be used in accordance with all aspects of the invention.

The catheter 10 of FIG. 1 has formed across the distal opening 16 a thin protective membrane 22. The membrane 22 is made from a soluble, bio-absorbable material such as polyethylene glycol. Although polyethylene glycol is a preferred material choice, other suitable materials may be used including gelatin, methyl cellulose, polyvinyl alcohol, polyethylene oxide, and polyvinyl pyrrolidone. The main criteria in choosing a suitable material for the protective membrane 22 for covering the distal opening 16 (and thereby protecting the main fluid lumen 12) are the capabilities of softening and eventually dissolving when in the presence of aqueous fluids such as those found in the body. Of course, only certain materials may be safely dissolved in certain regions of the body. For example, certain wax-based materials, such as paraffin, are not completely absorbed in the lung environment of the body and are therefore not suitable for pulmonary applications of the present device. Other materials which are not completely absorbed by the body and are therefore only suitable for non-pulmonary applications include bees wax, plastic materials including: polyethylene, polyvinyl chloride, and polyurethane; and inert biocompatible metal foils such as aluminum. Polyethylene glycol does completely dissolve and is therefore a preferred material for catheters used at least in the lung environment.

In accordance with a first embodiment of the invention, the protective membrane 22 is applied to the catheter 10 across the distal opening 16 by dipping the distal tip of the catheter 10 into a fluid state solution of the chosen membrane material, such as polyethylene glycol. The preferred protective membrane 22, which extends across the distal opening 16, is of a relatively uniform prescribed thickness, as shown in FIG. 1. A preferred thickness of the membrane 22 is about 0.020 inches.

To prevent the polyethylene glycol, when in its fluid state, from being drawn past the distal opening 16 and into the main fluid lumen 12, an "air mold" (a trapped volume of air) is established within the main fluid lumen 12. The air mold is created by capping or otherwise closing off the proximal main fluid conduit 18 with a suitable stopcock plug 24 prior to dipping the catheter 10 into the membrane solution. The stopcock plug 24, when closed, effectively traps air located within the main fluid lumen 12 as the distal end of the catheter 10 is dipped. The resulting "cushion" of air formed within the main fluid lumen 12 resists any proximal intrusion of the polyethylene glycol into lumen 12 as pressure increases slightly and as the catheter distal tip is dipped. The polyethylene glycol may only solidify into a film at the "boundary" between the air within the main fluid lumen 12 and the surface of the solution. This promotes a thin membrane 22 to be formed across the distal opening 16 of the catheter 10.

The physical phenomenon of capillary action of a fluid in contact with a tubular structure having micro-dimensions (such as tubes having inner diameters of up to about 0.08 inches) would greatly encourage the flow of liquid polyethylene glycol into the main fluid lumen 12 of the catheter in the absence of the cushion of air trapped within the main fluid lumen 12. The above described cushion of air trapped within the main fluid lumen 12 of the catheter 10 prevents substantially any polyethylene glycol from entering past the distal opening 16 due to capillary or other fluid action.

Figure 2:
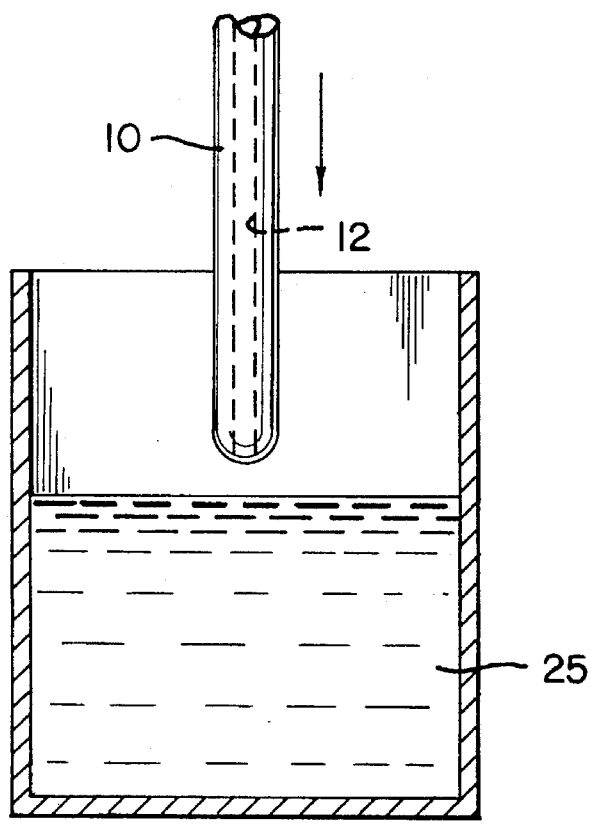
FIG. 2 is a conceptual schematic of a catheter in positioned prior to being dipped into hot pot filled with a membrane-forming liquid, in accordance with the invention.
Figure 3:
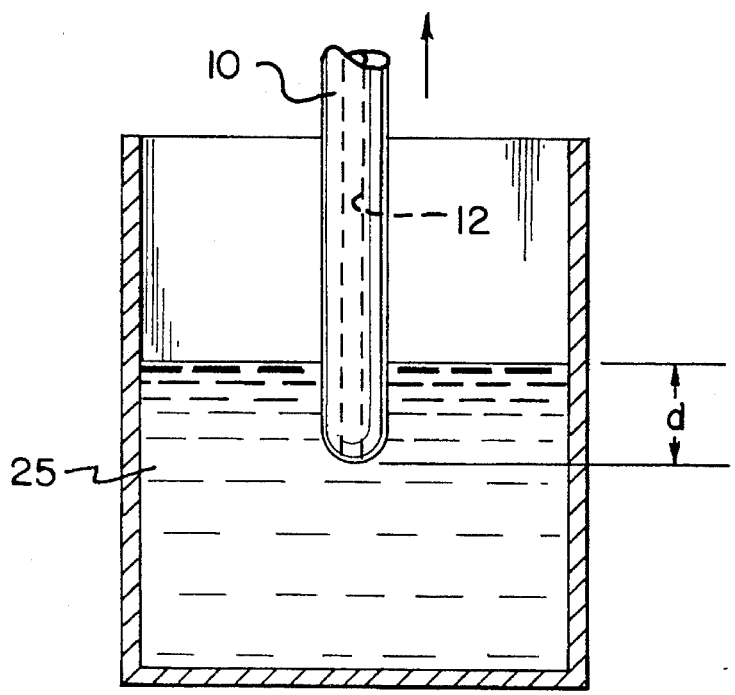
FIG. 3 illustrates the arrangement of FIG. 2 wherein the catheter is immersed beneath the membrane-forming liquid, in accordance with the invention.

As illustrated in FIGS. 2 and 3, once the proximal main fluid conduit 18 is sealed by the stopcock plug 24, the distal tip of the catheter 10 is immersed into the polyethylene glycol along a vertical axis lying perpendicular to the surface of the liquid 25.

To encourage the polyethylene glycol to quickly form a protective membrane across the distal opening 16, the temperature and, therefore, viscosity of the material is suitably controlled using a thermostatically controlled hot-pot operating approximately within the range between 90 and 120 degrees F. Suitable temperatures for other materials may be easily determined without undue experimentation.

The amount of trapped air within the main fluid lumen 12, the temperature of the polyethylene glycol (which directly determines the viscosity of the molten protective liquid 25), the depth (d) and the duration of the immersion as well as the number of successive immersions all together govern the thickness of the resulting protective membrane 22 (or laminate membrane).

After each dipping, the catheter 10 is quickly removed from the molten polyethylene glycol solution and allowed to cool in air. As a final step, the stopcock plug 24 is turned open and then removed from the catheter 10. A cap may be positioned over the proximal opening 19 (replacing the stopcock plug 24) to help minimize contamination to the otherwise noncritically contaminated main lumen of the catheter 10 until the catheter 10 is used.

The amount of air trapped within the main fluid lumen 12 of the catheter 10 during the above-described immersion step may be precisely reduced so that the actual position of the "air/liquid interface" recedes into the main fluid lumen 12, thus allowing the molten polyethylene glycol to pass further through the distal opening 16 to form a thicker membrane 22.

The predetermined release of air will effectively draw the air/liquid interface further up the main fluid lumen 12, during immersion. This retreat of the air/liquid interface will allow the polyethylene glycol to advance further up the main fluid lumen 12 during immersion and thereby form a thicker membrane 22. The predetermined release of air may be provided by a plug having a calibrated opening through which air may escape at a predetermined rate with respect to internal pressure. When relying on the predetermined release of air from the main fluid lumen 12 to accurately control the thickness of the membrane 22, the depth of immersion and the time of immersion becomes critical and must be carefully regulated.

The preferred method of forming the membrane across the distal opening 16 includes the following steps:

1. Occluding the proximal end of the main fluid lumen of a catheter with a plug having a passageway which may be capped or otherwise sealed, such as a stopcock valve;
2. Heating a container of polyethylene glycol to a temperature between 90 and 120 degrees Fahrenheit;
3. Immersing the distal opening of the fluid lumen of the catheter into the molten polyethylene glycol, moving the catheter along an axis which is perpendicular to the surface of the polyethylene glycol;
4. Removing the distal end of the catheter from the molten polyethylene glycol;
5. Allowing the newly formed membrane to cool and solidify in place across the distal opening of the fluid lumen;
6. Repeating steps 3–5 until a membrane having a desired thickness is formed across the distal opening; and
7. Removing the plug from the proximal end of the fluid lumen by first opening the passageway in the plug (either removing the cap or opening the stopcock valve) so that no negative pressure is created in the lumen which may damage the newly formed membrane.

EXAMPLE I

To produce a 0.020 inch thick imperforate membrane on a polyurethane balloon-tipped catheter, the following steps are performed:

1. Occlude the proximal end of the main fluid lumen of the catheter with a plug tapered to fit a standard female luer lock and having a ⅛ inch diameter passageway through its entire length. The external end of the passageway being adapted to receive a removable cap.
2. Heat the polyethylene glycol in a thermostatically controlled hot pot to a temperature of about 100 degrees Fahrenheit. Maintain this temperature.
3. Place the distal end of the catheter having a 0.038 inch inner diameter and a 0.091 inch outer diameter in a fixture which maintains the catheter in a vertical position, perpendicular to the surface of the polyethylene glycol.
4. Immerse the distal end of the fluid lumen of the catheter into the molten polyethylene glycol to a depth of about 0.02 inches for approximately three (3) seconds to form a membrane across the opening having approximately 0.02 inches thick. A deeper immersion, for example, to 0.12 inches will result in a thicker membrane.
5. Remove the catheter from the molten polyethylene glycol and allow it to air cool for about two (2) minutes so that the newly formed membrane completely solidifies.
6. Remove the plug by first carefully prying the cap from the external end of the passageway of the plug. As the plug is removed from the proximal end of the catheter air is allowed to enter the main fluid lumen through the now open passageway and equilibrate the air pressure within the fluid lumen. The open passageway of the plug prevents the creation of a vacuum which can rupture or otherwise damage the delicate membrane.

In accordance with another embodiment of the invention, referring to FIGS. 4 through 8, the above-described membrane 22 is formed across the distal opening of the catheter 10 using a closely fitted mandrel 26 positioned within the main lumen 12. The mandrel 26 is shaped to extend in the main fluid lumen 12 up to the distal end and through the distal opening 16 a prescribed distance. The mandrel 26 essentially functions as a solid mold, replacing the cushion of trapped air used in the above-described embodiment, to provide a mold surface 28 along which the molten membrane solution may solidify to form membrane 22 having a predetermined thickness. The exact dimensions of the mandrel 26 described above and herein after are dependent on the exact dimensions of the main fluid lumen 12 of the catheter 10. The main criteria of the mandrel are that it fits snugly within the fluid lumen 12 of the catheter, that it may be easily removed, and that it may be slid sufficiently forward within the fluid lumen 12 to function as a mold for producing the distal end membrane 22, in accordance with the invention.

Figure 4:
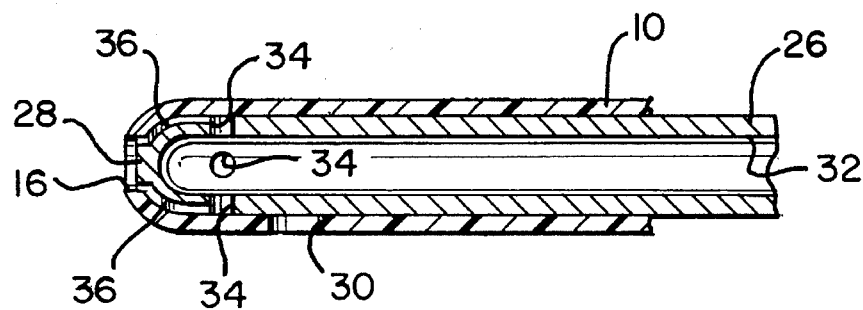
FIG. 4 is a partial, sectional view of a hollow mandrel in position within the fluid lumen of a catheter, in accordance with another embodiment of the invention.

The catheter 10 shown in FIG. 4 includes, as an illustration of the various types of catheters, a side-wall portal opening 30 in addition to the forward-facing distal opening 16. A catheter having a portal opening 30 may be similarly coated with an appropriate membrane material, as described above, when fitted with a mandrel 26, as shown in FIG. 4 (and FIG. 7, as discussed in greater detail below).

Figure 5:
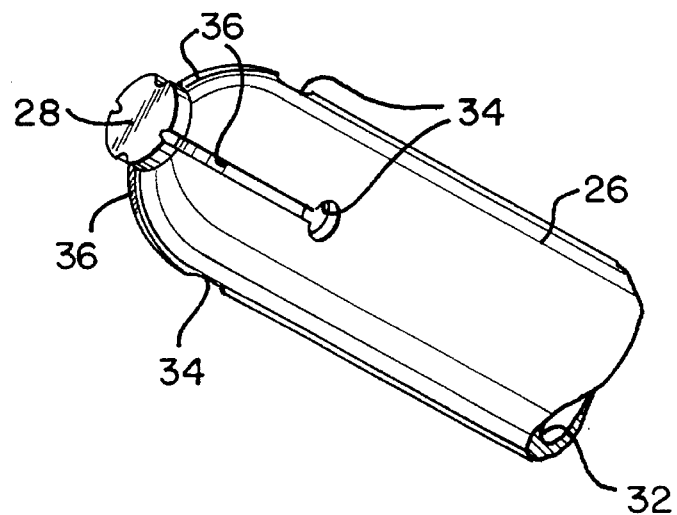
FIG. 5 is a perspective view of the distal end of the hollow mandrel of FIG. 4 showing details of side ports and channels.
Figure 6:
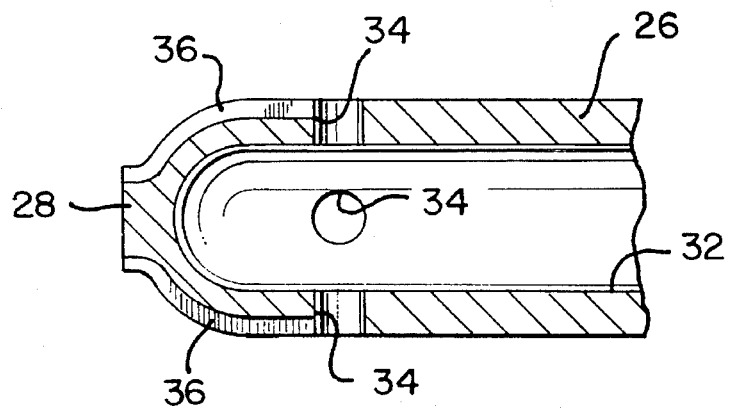
FIG. 6 is a partial, sectional view of the distal end of the hollow mandrel of FIG. 4.

In one version, referring to FIGS. 4 through 6, the mandrel 26 is hollow and includes a central passage 32, side ports 34 and exterior channels 36. The side ports 34 are preferably positioned equidistant about the circumference of the mandrel 26, near its distal end, and connect with proximal ends of respective exterior channels 36. The channels 36 extend from respective side ports 34, tapering forward, to the mold surface 28, as shown in FIGS. 5 and 6. The central passage 32, the side ports 34, and the exterior channels 36 serve two similar functions; to allow any air that is trapped adjacent the mold surface 28 during immersion of the catheter 10 to escape, and to allow air to flow into the space between the newly formed membrane 22 and the mold surface 28 as the mandrel 26 is drawn from the catheter 10.

In another version of the mandrel 26, as shown in FIGS. 7 and 8, the mandrel 26 is solid and includes a mold surface 28 and preferably three or four striations 38 evenly formed along the length of the mandrel 26. The striations 38 establish channels 40 therebetween which extend along the length of the mandrel 26 to the mold surface 28. The channels 40 allow air to communicate between the inner side of a newly formed membrane 22 and the atmosphere, thereby preventing premature membrane damage and/or deformation. The striations 38 are preferably sufficiently wide to cover a portal opening 30, where appropriate. The outermost surface 41 of the striations 38 (one or more) serve as mold surfaces 28, allowing the membrane 22 to solidify across each portal opening 30.

Both of the above-described versions of the mandrel 26 may be rigid or flexible and may be made from an appropriate metal or from a lubricous plastic, such as NYLON or TEFLON. As will be understood by one of ordinary skill in the art, the mandrel may be made having the cross-sectional shape of the fluid lumen 12 by any appropriate extrusion process such as the extrusion process used to manufacture the catheter itself.

With an appropriate mandrel 26 positioned in the main fluid lumen 12 of a catheter 10, the distal end of the catheter 10 may be immersed into the desired liquid membrane solution as described above and illustrated in FIGS. 2 and 3. The solution will quickly solidify within the pocket formed by the distal opening 16 and the mold surface 28 of the inserted mandrel 26. Alternatively, the membrane solution may be sprayed or otherwise applied to the distal opening 16 against the mold surface 28 of the mandrel 26 to form the membrane 22.

Once the membrane 22 has solidified across the distal opening 16 of the catheter 10, the mandrel 26 may be removed from the main fluid lumen 12. It is important that the mandrel 26 is removed in such a manner, as described in the above described example 1 and the preferred process (i.e., use of a plug having a passageway and a removable cap or a stopcock), to prevent rupturing the newly formed membrane 22. Prior to removing, the mandrel 26 is preferably first rotated within the main lumen 12 to ensure that any surface bond formed between the membrane 22 and the mold surface 28 is safely broken.

In use, a catheter 10 having a polyethylene glycol protective barrier or membrane 22 formed across a distal opening 16 is routed through a patient to a desired site in any conventional manner. When it is necessary to establish fluid communication to and from the site through the main fluid lumen, the membrane 22 (if not already dissolved) must be ruptured. Depending on the location of the particular site within the patient, a controlled volume of either air or an appropriate liquid may be forced through the main fluid lumen 12 to rupture the membrane 22. Any fragments of the ruptured membrane 22 will be readily absorbed or expelled by the body and will cause no harm.

The method used to apply the above-listed plastic materials and wax-base materials such as (paraffin wax or bees wax) across the distal opening of a catheter is identical to the above-described method for applying the polyethylene glycol. The temperature of the hot pot must be raised to within the range of about 90 to 120 degrees Fahrenheit to obtain a desired molten state of the material when using material such as polyethylene glycol, bees wax, and paraffin wax. For other materials such as plastics, it may be necessary to heat the material up to about 300 degrees Fahrenheit. Determination of the particular temperatures required to maintain appropriate molten viscosity of which ever material is used is well within the capability of persons of ordinary skill in the art without undue experimentation.

The above-described method for rupturing fully soluble membranes 22 may be similarly applied to the rupturing of insoluble membranes. Once ejected from the main fluid lumen 12 of the catheter 10, the insoluble membrane 22 will be naturally expelled from the body, if used where the body may easily and safely expel the insoluble material, such as in the large intestine.

In addition to the above-described methods for forming a thin membrane across a distal opening 16 of a catheter 10, a pre-formed membrane material may also be used. Here, each membrane 22 is precut from uncoated or adhesive-coated elastomeric film, plastic film, or metal foil. The precut membrane 22 having the adhesive may be bonded to the catheter 10, across the distal opening 16, using an appropriate adhesive or any other suitable solvent, dielectric, ultrasonic, infrared or any other manner of attaching the membrane to the catheter tip.

Referring to FIG. 9, an alignment device 50 is shown for aligning and holding a precut membrane 22 in place with respect to an inserted catheter 10 until an appropriate bond is established. A mandrel 26, such as the one disclosed in FIG. 4 and discussed above, is inserted into the main fluid lumen 12 of the catheter 10. Together, the distal end of the catheter 10 and the mandrel 26 is inserted into an opening provided by the alignment device 50. The alignment device 50 is essentially a female mold which automatically positions a precut membrane 22 within the distal opening 16 of the inserted catheter 10 and forces it up against the flat mold surface 28 of the mandrel 26. After the appropriate bonding treatment is applied to the alignment device 50 which causes the precut membrane 22 to adhere and set to the catheter 10, the catheter and the inserted mandrel 26 may be removed from the alignment device 50 and the mandrel 26 removed from the catheter 10.

Precut membranes 22 having no adhesive coating may be adhered to the catheter 10 across the distal opening 16 using any appropriate adhesive, such as a cyanoacrylate adhesive (CA glue). Here, after a mandrel 26 is inserted into the fluid lumen 12 of the catheter 10, a wiping device applies a thin coat of the CA glue across the distal opening 16. The catheter 10 is lowered along a vertical axis (or at least perpendicular to the awaiting precut membrane 22) into mating contact with a precut membrane 22. The membrane 22 is immediately adhered to the catheter 10 across the distal opening 16. After the bond has set, the mandrel 26 is removed from the fluid lumen 12.

Referring to FIG. 10, another embodiment of the invention is shown, including a catheter 10 having at least one fluid lumen 12 extending from a proximal opening 19 to a distal opening 16. The proximal opening 19 may include any of several conventional end connectors, but preferably a standard luer-lock connector 52.

Figure 12:
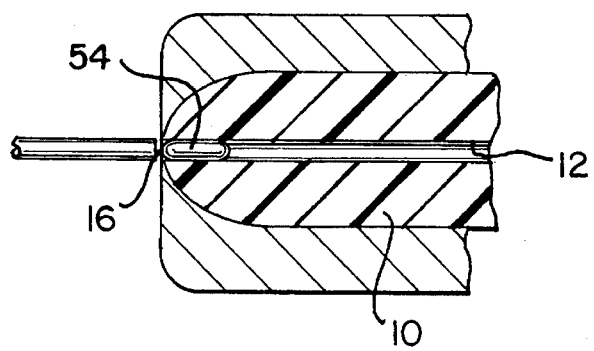
FIG. 12 is a partial, sectional side view of a catheter having a rod shaped sealing plug located in its fluid lumen, in accordance with yet another embodiment of the invention.
Figure 13:
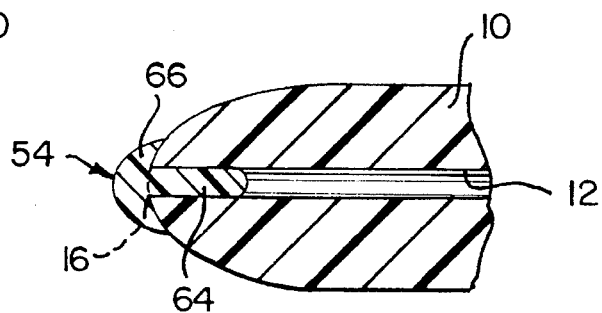
FIG. 13 is a partial, sectional side view of a catheter having a contoured shaped sealing plug located within its distal opening, in accordance with another embodiment of the invention.

In accordance with this embodiment, an imperforate sealing plug 54 is positioned into the distal opening 16 of the fluid lumen 12. The sealing plug 54 functions in place of the above-described membrane 22. The sealing plug 54 is preferably made from a soluble or insoluble bio-compatible material and may be spherically shaped as a pellet (as shown in FIG. 10), rod shaped (as shown in FIG. 12) or contoured like a thumb-tack, for example (having substantially a "T" cross-section as shown in FIG. 13).

The sealing plug 54, regardless of its shape, is used to occlude the distal opening 16 end of the fluid lumen 12 of the catheter 10. The sealing plug is similar to the above-described sealing membrane 22 in that by occluding the distal opening 16 of the catheter 10 using either the sealing plug 54 or the membrane 22, the previous problems of the prior art, including tissue "coring" and contamination, are avoided.

Referring to FIG. 10, a first version of the sealing plug 54 is illustrated in place within the fluid lumen 12 of a catheter 10. The pellet shaped sealing plug 54 is a spherical bead made from any of the above-listed bio-compatible soluble or insoluble materials. The size of the pellet shaped sealing plug 54 depends on the size of the fluid lumen 12 of the catheter 10. The diameter of the pellet should be slightly larger than the diameter of the fluid lumen 12 so that, when inserted, the pellet fits snugly into the fluid lumen 12, adjacent the distal opening 16.

Figure 11A:
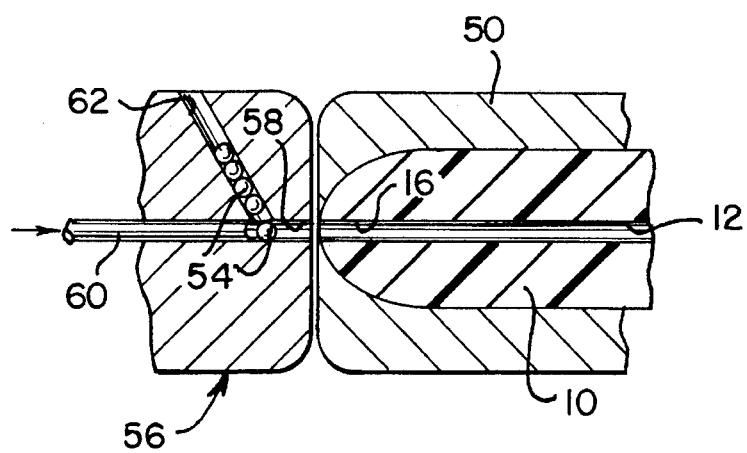
FIG. 11a is a partial, sectional side view of a catheter adjacent a loading device prior to receiving a pellet shaped sealing plug.
Figure 11B:
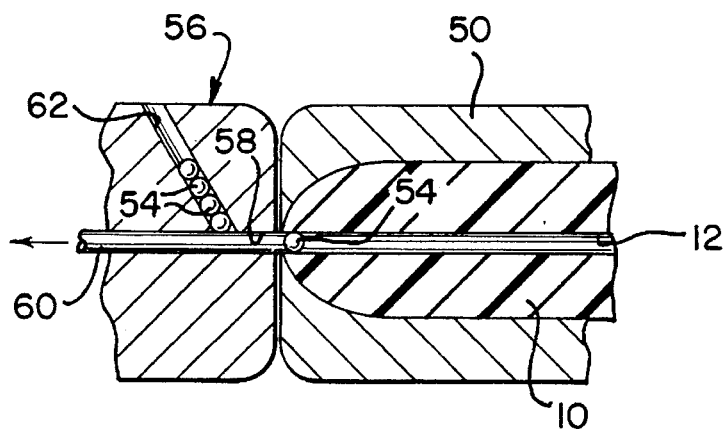
FIG. 11b is a partial, sectional side view of a catheter adjacent the loading device receiving a pellet shaped sealing plug.

In accordance with another embodiment of the invention, the pellet shaped sealing plug 54 is inserted into the catheter 10 using a pellet loader 56, as shown in FIGS. 11a and 11b. A catheter 10 is positioned with its distal opening 16 adjacent the outlet of the pellet loader 56. The loader 56 includes a barrel 58, a piston 60 and a supply hopper 62 of pellets. The piston 60 moves from a retracted position shown in FIG. 11a to an extended position, shown in FIG. 11b, forcing a single pellet shaped sealing plug 54 into the fluid lumen 12 of an awaiting catheter 10. As the piston 60 retracts, another pellet from the hopper 62 automatically enters the barrel 58. The depth of pellet penetration into the fluid lumen 12 may be easily controlled by regulating the throw of the piston. Depending on the application and the desired level of barrier protection, additional pellets may be subsequently inserted into the same catheter 10.

The pellets may be manufactured using any appropriate conventional process including molding each pellet or a run of pellets at once using a mold. The pellets may also be made as spheres using a conventional free-fall, quick-chill process wherein measured molten beads are dropped in a cooling shaft and allowed to solidify as spheres.

Referring to FIG. 12, the sealing plug 54 is rod shaped. A rod from a stock length supply is inserted into the fluid lumen 12 of a catheter 10 a predetermined distance. The rod is then cut flush with the rim of the distal opening 16.

The rod material used as the sealing plug 54 may be formed by extruding a first material to match the cross-section of the main fluid lumen of the particular catheter. The formed extruded rod may then be coated with a second material, e.g., polyethylene glycol, polyvinyl alcohol or any other similar soluble biocompatible material. The second material may be applied to the extruded first material through known spraying, atomizing, or similar processes or by standard dipping techniques.

The purpose of the coating is to provide a softer more pliable layer to the exterior of the relatively harder core of the extruded first material. The softer coating allows a tight seal to be formed within the fluid lumen of the catheter, while the harder core provides the necessary structural integrity of the sealing plug 54.

As shown in FIG. 13, the sealing plug 54 is contour-shaped, preferably having a somewhat "T" cross-section similar to a thumb tack with a rounded head. A shaft 64 having a prescribed length of the "T" sealing plug 54 is inserted into the fluid lumen 12 of a catheter 10 until a cap portion 66 of the sealing plug 54 abuts evenly with the rim of the distal opening 16. The shaft 64 functions to secure the sealing plug 54 in place within the fluid lumen 12. The contoured cap portion 66 functions to cover the rim of the distal opening 16 preventing tissue from forcing the sealing plug 54 further up the fluid lumen 12. In addition, the contoured cap 66 more effectively and less traumatically passes through internal body tissues during insertion of the catheter.

As discussed above, any one of the above-mentioned embodiments of the invention may be employed with any type of body entering catheter or body piercing device (e.g., a trocar). It is also contemplated that a protective barrier plug or membrane may be inserted into or formed across the distal opening of the fluid channel of a bronchoscope. With this arrangement, virtually no contaminated material located within the patient's body will enter the fluid channel of the bronchoscope, and therefore the later inserted catheter will also remain substantially contamination free when it passes through the fluid channel of the bronchoscope and to the desired site.

Furthermore, it is also contemplated that a controlled flow of air or liquid be forced through the fluid channel as the bronchoscope is fed through the passageways of the patient's body. The pressure developed by the forced fluid prevents any material from entering the fluid channel, resulting in a substantially contamination free passageway to the infected site to be studied. This fluid pressurized system functions as a protective barrier to the fluid channel of the bronchoscope.

What is claimed is:

1. A catheter which is to be atraumatically advanced through potentially contaminated material within a body lumen of a patient to a desired site, said catheter having distal and proximal ends and comprising:

a fluid lumen extending between said distal end and said proximal end, said fluid lumen having a distal facing opening at said distal end and providing fluid communication between said site and said proximal end when said distal end is at said site, said distal end of said catheter being blunt; and a removable protective barrier positioned across said distal facing opening of said fluid lumen at said distal end, said protective barrier being made from a bio-compatible material and occluding said distal end of said fluid lumen thereby preventing entry of said contaminated material prior to said distal end of said catheter reaching said desired site, said protective barrier being selectively removable by fluid pressure in said lumen exceeding a predetermined level, said protective barrier being blunt.

2. The catheter according to claim 1, wherein said protective barrier is made from a material which is soluble in the patient's own body fluids.

3. The catheter according to claim 2, wherein said protective barrier is made from polyethylene glycol.

4. The catheter according to claim 2, wherein said protective barrier is made from gelatin.

5. The catheter according to claim 2, wherein said protective barrier is made from methyl cellulose.

6. The catheter according to claim 2, wherein said protective barrier is made from polyvinyl alcohol.

7. The catheter according to claim 2, wherein said protective barrier is made from polyethylene oxide.

8. The catheter according to claim 2, wherein said protective barrier is made from polyvinyl pyrrolidone.

9. The catheter according to claim 1, wherein said protective barrier is made from an insoluble material.

10. The catheter according to claim 9, wherein said protective barrier is made from bees wax.

11. The catheter according to claim 9, wherein said protective barrier is made from paraffin wax.

12. The catheter according to claim 9, wherein said protective barrier is made from a metal foil.

13. The catheter according to claim 9, wherein said protective barrier is made from an elastomeric material.

14. The catheter according to claim 13, wherein said elastomeric material is rubber.

15. The catheter according to claim 9, wherein said protective barrier is made from a plastic film.

16. The catheter according to claim 1, wherein said sealing protective barrier is a sealing plug that is spherical in shape and located within said fluid lumen.

17. The catheter according to claim 1, wherein said sealing protective barrier is a sealing plug that is rod shaped.

18. The catheter according to claim 1, wherein said sealing protective barrier comprises a head portion and a shaft portion, said head portion being generally rounded, said shaft portion being sized to fit within and engage said fluid lumen to retain said head portion against said catheter distal end.

19. A catheter in accordance with claim 1, wherein said protective barrier is a flat film, the thickness of said film and the material of which it is made being selected so that said film will rupture when said fluid pressure exceeds said predetermined level.

20. A catheter in accordance with claim 19, further comprising means located at said proximal end of said catheter for applying said fluid pressure in said lumen sufficient in magnitude to remove said barrier from said lumen.

* * * * *